(12) United States Patent
Kuzma et al.

(10) Patent No.: US 7,315,763 B2
(45) Date of Patent: Jan. 1, 2008

(54) COCHLEAR IMPLANT ELECTRODE AND METHOD OF MAKING SAME

(75) Inventors: Janusz A. Kuzma, Parker, CO (US); Lani A. Smith, Parker, CO (US); Chuladatta Thenawara, Castaic, CA (US); Steven A. Hazard, Castaic, CA (US)

(73) Assignee: Advanced Bionics Corporation, Valencia, CA (US)

( * ) Notice: Subject to any disclaimer, the term of this patent is extended or adjusted under 35 U.S.C. 154(b) by 532 days.

(21) Appl. No.: 10/666,465

(22) Filed: Sep. 19, 2003

(65) Prior Publication Data

US 2004/0127968 A1    Jul. 1, 2004

Related U.S. Application Data

(60) Provisional application No. 60/412,253, filed on Sep. 19, 2002.

(51) Int. Cl.
*A61N 1/05*    (2006.01)
(52) U.S. Cl. ..................................... 607/137
(58) Field of Classification Search ............ 607/2, 607/55, 137, 57, 116–119; 600/373–379
See application file for complete search history.

(56) References Cited

U.S. PATENT DOCUMENTS

| | | | |
|---|---|---|---|
| 4,284,085 A | | 8/1981 | Hansen et al. |
| 4,357,497 A | * | 11/1982 | Hochmair et al. ............. 607/5 |
| 4,532,930 A | | 8/1985 | Crosby et al. |
| 4,819,647 A | * | 4/1989 | Byers et al. ................ 607/116 |
| 5,092,333 A | * | 3/1992 | Tsuchida et al. ............. 600/395 |
| 5,324,321 A | * | 6/1994 | Pohndorf et al. ........... 607/116 |
| 5,443,493 A | | 8/1995 | Byers et al. |
| 5,545,219 A | | 8/1996 | Kuzma |
| 5,578,084 A | | 11/1996 | Kuzma et al. |
| 5,603,726 A | | 2/1997 | Schulman et al. |
| 5,630,839 A | | 5/1997 | Corbett, III et al. |
| 5,645,585 A | | 7/1997 | Kuzma |
| 5,649,970 A | | 7/1997 | Loeb et al. |
| 5,653,742 A | | 8/1997 | Parker et al. |
| 5,776,178 A | | 7/1998 | Pohndorf et al. |
| 6,038,484 A | | 3/2000 | Kuzma |
| 6,070,105 A | | 5/2000 | Kuzma |

(Continued)

FOREIGN PATENT DOCUMENTS

WO    WO9710784 A1    3/1997

(Continued)

*Primary Examiner*—George R. Evanisko
(74) *Attorney, Agent, or Firm*—Philip H. Lee; Victoria A. Poissant

(57) ABSTRACT

A cochlear stimulation lead having a pre-curved electrode array is provided. The molding process provides memory to the curved part of the lead. The lead may be made having a stylet insertion channel that extends from a slightly curved or substantially straight section and into the highly curved section of the lead. Because high compliance is desired for the lead in cochlear stimulation applications, the compliance is controlled not only by the taper at the distal end of the lead and overall lead thickness, but also by choosing the material hardness of the lead carrier/covering and employing compliant zigzagged conductor wire. In addition, differential lead compliance/stiffness can be achieved by using a stiff tubing that forms part of the stylet insertion channel.

6 Claims, 12 Drawing Sheets

U.S. PATENT DOCUMENTS

| | | | |
|---|---|---|---|
| 6,119,044 A * | 9/2000 | Kuzma | 607/137 |
| 6,125,302 A | 9/2000 | Kuzma | |
| 6,144,883 A | 11/2000 | Kuzma | |
| 6,149,657 A * | 11/2000 | Kuzma | 606/129 |
| 6,195,586 B1 | 2/2001 | Kuzma | |
| 6,266,568 B1 * | 7/2001 | Mann et al. | 607/137 |
| 6,304,787 B1 | 10/2001 | Kuzma et al. | |
| 6,421,569 B1 | 7/2002 | Treaba et al. | |
| 7,044,942 B2 * | 5/2006 | Jolly et al. | 604/891.1 |
| 7,146,227 B2 | 12/2006 | Dadd et al. | |
| 2002/0019669 A1 * | 2/2002 | Berrang et al. | 623/10 |
| 2003/0045921 A1 | 3/2003 | Dadd et al. | |
| 2004/0030376 A1 | 2/2004 | Gibson et al. | |
| 2004/0078057 A1 | 4/2004 | Gibson | |
| 2004/0116995 A1 | 6/2004 | Dadd | |
| 2004/0122501 A1 * | 6/2004 | Dadd et al. | 607/137 |

FOREIGN PATENT DOCUMENTS

| | | |
|---|---|---|
| WO | WO 00/71063 A1 | 11/2000 |
| WO | WO 02/32498 A1 | 4/2002 |

* cited by examiner

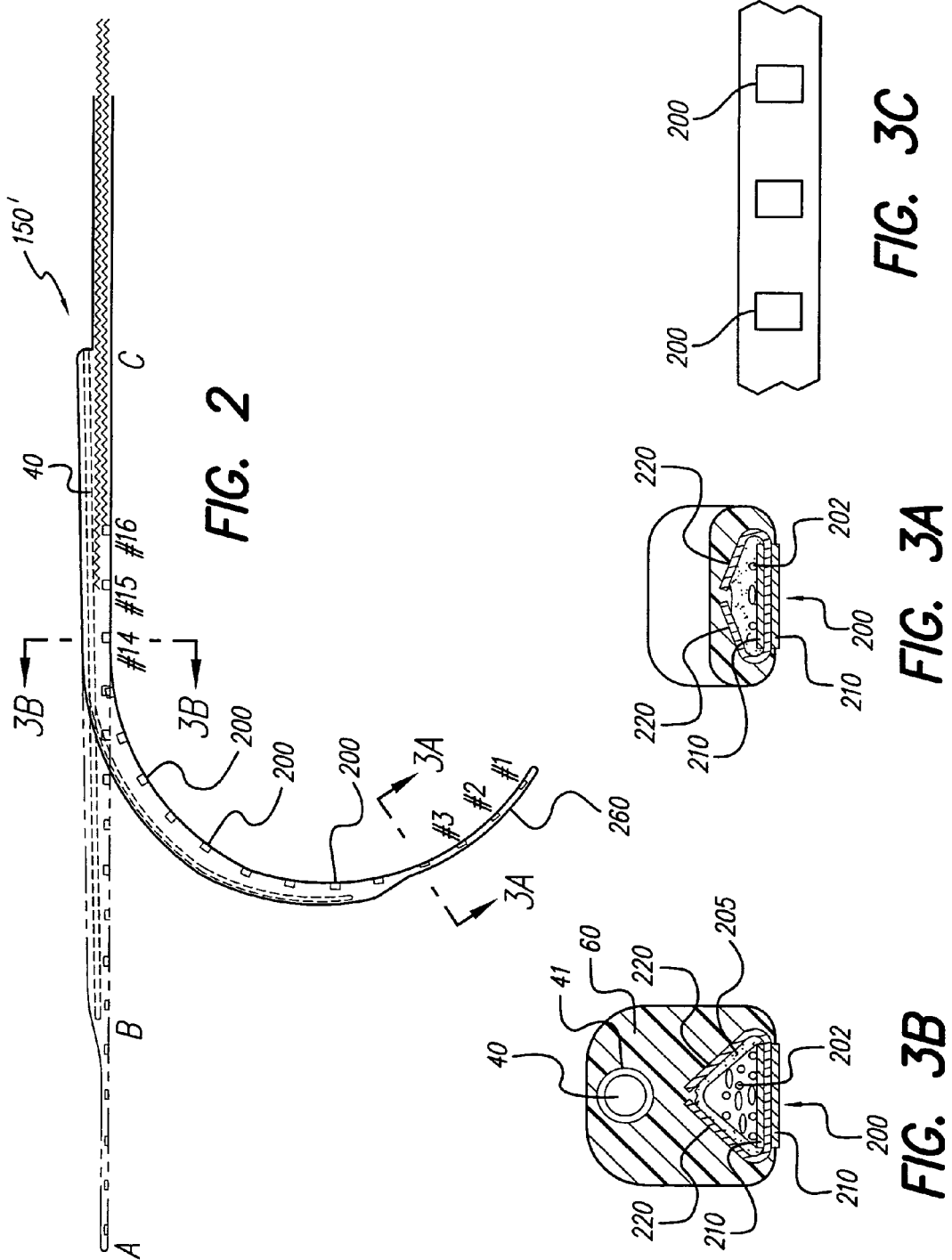

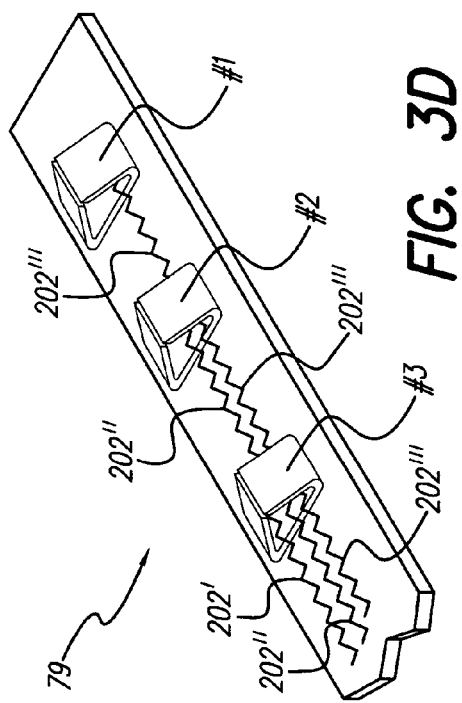
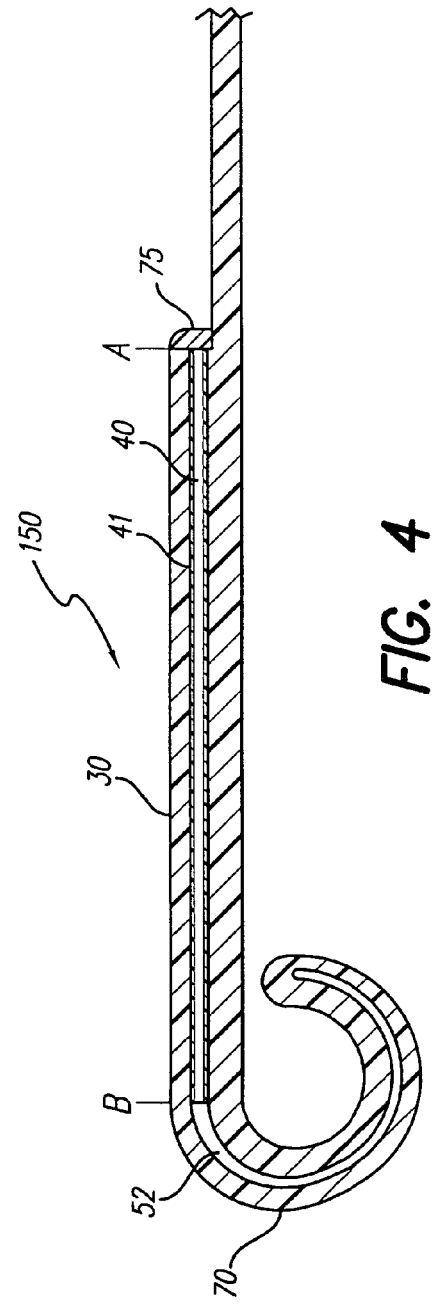

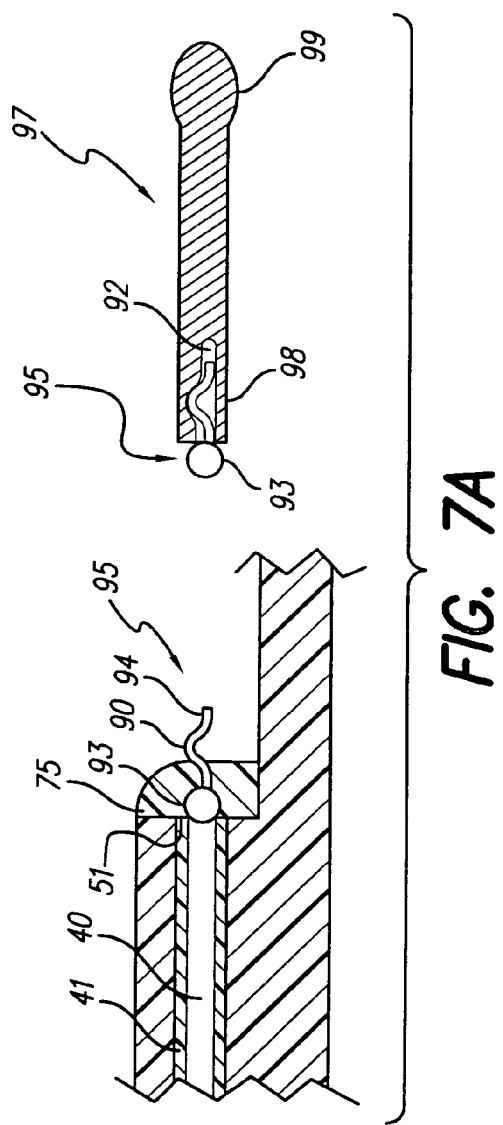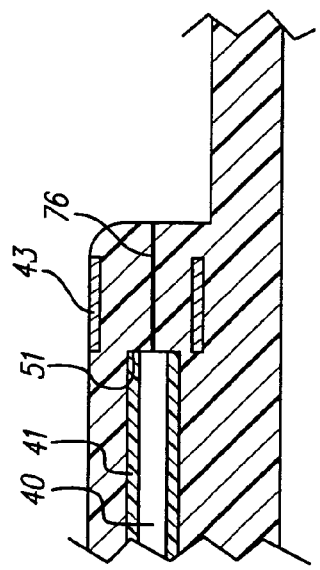
FIG. 7A
FIG. 7B

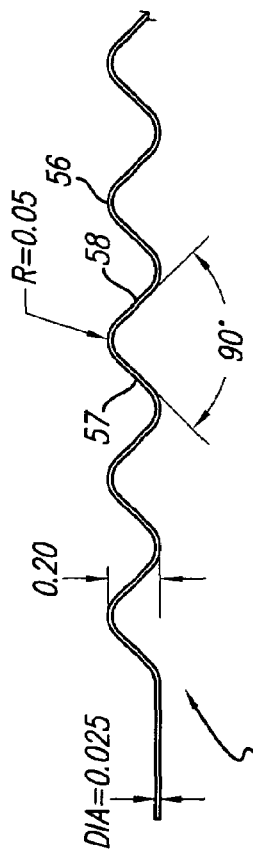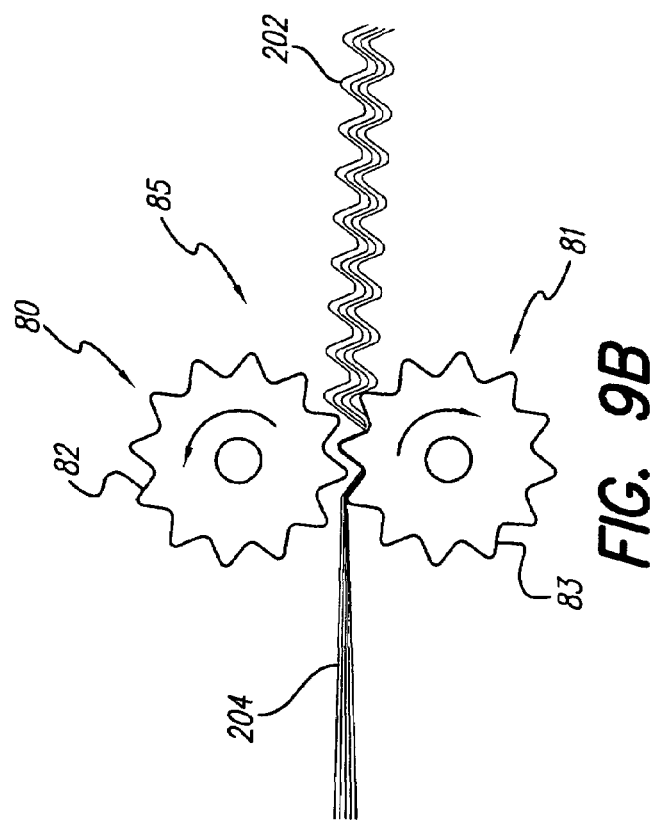

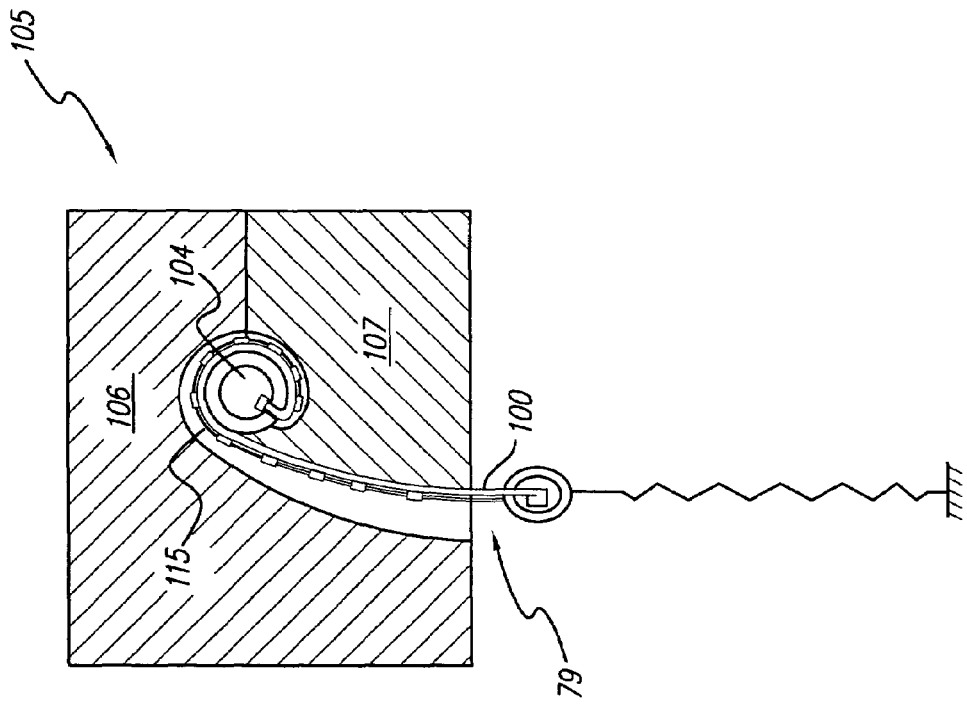
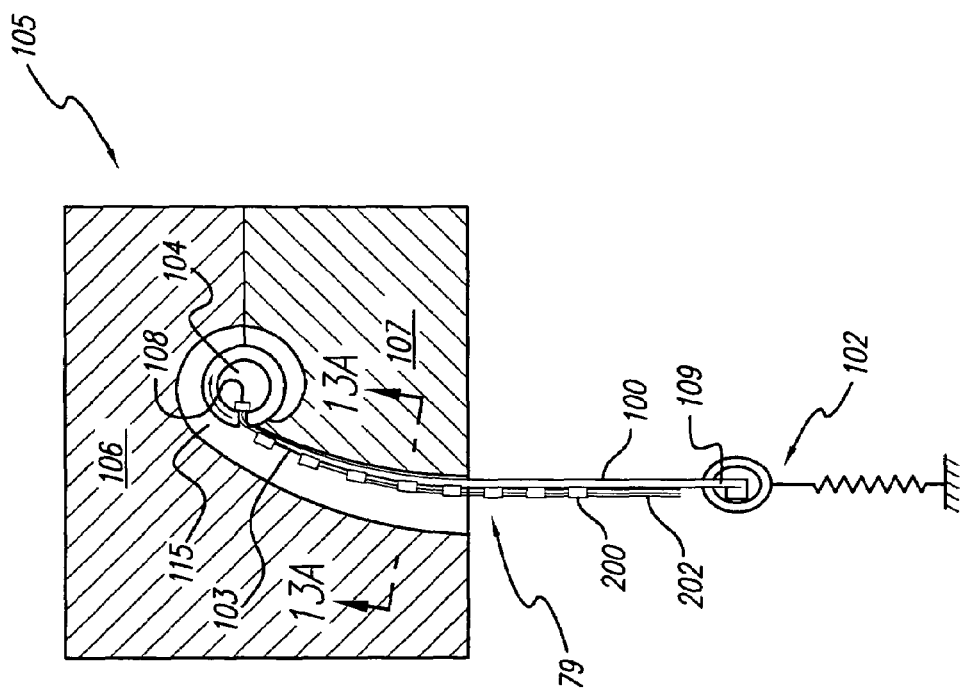

COCHLEAR IMPLANT ELECTRODE AND METHOD OF MAKING SAME

The present application claims the benefit of U.S. Provisional Patent Application Ser. No. 60/412,253, filed 19 Sep. 2002, which application is herein incorporated by reference.

BACKGROUND OF THE INVENTION

The present invention relates to implantable stimulation devices, and, more particularly, to electrode arrays for stimulation of the cochlea. Electrode arrays consist of electrode contacts generally placed along one side of an elongate carrier so that when the array is implanted within one of the cochlear ducts such as the scala tympani, the electrode contacts are positioned in close proximity to the cells that are to be stimulated, allowing such cells to be stimulated with minimal power consumption.

For purposes of clarity, as used herein, an implantable stimulating lead is a device that has one or more electrode contacts that deliver current to tissue to be stimulated. An electrode contact is that part of the stimulating device which is actually electrically conductive and is in contact with the body tissue that is to be stimulated. The term "electrode" may sometimes be used narrowly as the electrode contact or contacts only and, other times, more broadly, as the electrode contact or contacts and all the surrounding structure, including the insulation carrier that the contacts are placed upon, as well as the conductor wires and any other assemblies within or on the insulation carrier. As used herein, the broad definition of the term "electrode" will be adopted, which includes the electrode contacts and all surrounding structures. In addition, when the term "lead" is used, it will be used interchangeably with the broad use of the term "electrode." The term "electrode array" will refer to that portion of the electrode or lead that includes all of the electrode contacts and the immediate structures upon which the electrode contacts are attached. Thus, the term "electrode array" may be narrower than the broad term "electrode" in that any carrier insulation and conductor wire that is not immediate to the electrode contacts will not be included in the term "electrode array."

Hearing loss, which may be due to many different causes, is generally of two types: conductive and sensorineural. Of these, conductive hearing loss occurs where the normal mechanical pathways for sound to reach the hair cells in the cochlea are impeded, for example, from damage to the ossicles. Conductive hearing loss may often be helped by using conventional hearing aids that amplify sounds so that acoustic information can reach the cochlea and the hair cells. Some types of conductive hearing loss are also amenable to alleviation by surgical procedures.

In many people who are profoundly deaf, however, the reason for their deafness is sensorineural hearing loss. This type of hearing loss can arise from the absence or the destruction of the hair cells in the cochlea which transduce acoustic signals into auditory nerve impulses. Individuals with sensorineural hearing loss are unable to derive any benefit from conventional hearing aid systems no matter how loud the acoustic stimulus is, because the mechanism for transducing sound energy into auditory nerve impulses has been damaged. Thus, in the absence of properly functioning hair cells, auditory nerve impulses cannot be generated directly from sounds.

To overcome sensorineural deafness, cochlear implant systems or cochlear prostheses have been developed, which can bypass the hair cells located in the vicinity of the radially outer wall of the cochlea by presenting electrical stimulation to the auditory nerve fibers directly. This leads to the perception of sound in the brain and provides at least partial restoration of hearing function. Thus, most of these cochlear prosthesis systems treat sensorineural deficit by stimulating the ganglion cells in the cochlear directly using an implanted electrode a or lead that has an electrode array.

A cochlear prosthesis operates by directly stimulating the auditory nerve cells, bypassing the defective cochlear hair cells that normally transduce acoustic energy into electrical activity to the connected auditory nerve cells. In addition to stimulating the nerve cells, the electronic circuitry and the electrode array of the cochlear prosthesis separate the acoustic signal into a number of parallel channels of information, each representing a narrow band of frequencies within the perceived audio spectrum. Ideally, each channel of information should be conveyed selectively to a subset of auditory nerve cells that normally transmits information about that frequency band to the brain. Those nerve cells are arranged in an orderly tonotopic sequence, from the highest frequencies at the basal end of the cochlear spiral to progressively lower frequencies towards the apex. In practice, however, this goal can be difficult to realize because of the particular anatomy of the cochlea.

Over the past several years, a consensus has generally emerged that the scala tympani, one of the three parallel ducts that make up the spiral-shaped cochlea, provides the best location for implantation of an electrode array used as part of a cochlear prosthesis. The electrode array to be implanted in the scala tympani typically can consists of a thin, elongated, flexible carrier containing several longitudinally disposed and separately connected stimulating electrode contacts, conventionally numbering about 6 to 30. Such an electrode array is pushed into the scala tympani duct in the cochlea to a depth of about 20-30 mm via a surgical opening made in the round window at the basal end of the duct.

In use, the cochlear electrode array delivers electrical current into the fluids and tissues immediately surrounding the individual electrode contacts to create transient potential gradients that, if sufficiently strong, cause the nearby auditory nerve fibers to generate action potentials. The auditory nerve fibers branch from cell bodies located in the spiral ganglion which lies in the bone or modiolus, adjacent to the inside wall of the scala tympani. Because the density of electrical current flowing through volume conductors such as tissues and fluids tends to be highest near the electrode contact that is the source of such current stimulation at one contact site tends to selectively activate those spiral ganglion cells and their auditory nerve fibers that are closest to that contact site. Thus, it is important generally for the electrode contacts to be positioned as close to the ganglion cells as possible. Conventionally, after implant, the electrode array consisting of electrode contacts should hug the modiolar wall (or inside wall of the scala tympani). When the electrode side of the array is positioned closest to the modiolar wall, the electrode contacts are on the medial side of the lead.

In order to address the above need, it is known in the art to make an intracochlear electrode array that includes a spiral-shaped, resilient carrier which generally has a natural, spiral shape so that the array better conforms to the shape of the scala tympani. See, e.g., U.S. Pat. No. 4,819,647, which is incorporated herein by reference. While the electrode array with a spiral-shaped carrier shown in the '647 patent represents a significant advance in the art, it lacks sufficient shape memory to allow it to return to its original curvature (once having been straightened for initial insertion) and to provide sufficient hugging force to wrap snugly against the modiolus of the cochlea.

It is also known in the art, as shown in U.S. Pat. Nos. 5,545,219 and 5,645,585, to construct an electrode carrier from two initially straight members, a rod-like electrode carrier and a flexible rod-like positioning member. The '219 and '585 U.S. patents are also incorporated herein by reference. As shown in these patents, the two members extend in substantially parallel relation to and closely alongside each other, but are connected to each other only at their respective leading and trailing ends. After implant, a pushing force is applied to the positioning member so that it is forced to assume an outwardly arched configuration relative to the electrode carrier, thereby forcing the electrode carrier into a close hugging engagement with the modiolus and placing the electrode contacts as close to the cells of the spiral ganglion as possible. The '219 patent, in particular, shows in FIGS. 1-10 and describes in the accompanying text an excellent summary of prior art electrodes and the deficiencies associated therewith. Other patents relevant to the subject matter of cochlear stimulation leads are: U.S. Pat. Nos.: 6,125,302; 6,070,105; 6,038,484; 6,144,883; and 6,119,044, which are all herein incorporated by reference.

While the electrode arrays taught in the above-referenced '219 and '585 patents are based on the correct goal, i.e., to force the electrode carrier into a close hugging engagement with the modiolus, it does so only by using an additional element that makes manufacture of the lead more difficult and expensive and only by applying an additional pushing force to an electrode structure after it has already been inserted into the cochlea. Such additional pushing force may cause damage to the delicate scala tympani or cause the electrode contacts to twist or to separate away from the modiolus, rather than be placed in the desired hugging relationship.

Thus, while it has long been known that an enhanced performance of a cochlear electrode or lead can be achieved by proper placement of the electrode contacts close to the modiolar wall of the cochlea, a major challenge has been obtaining a electrode/lead design that does not use excessive force to achieve this close placement. There has either been the need for application of an external and possibly unsafe force or a lack of sufficient shape memory to allow the electrode to assume or return to the desired curvature (after the electrode has been initially straightened during insertion) so that the electrode array wraps snugly around the modiolus of the cochlea.

It is thus evident that improvements are still needed to obtain a cochlear electrode that has shape memory, is easily implanted so that excessive force is not required, and can be easily manufactured.

SUMMARY OF THE INVENTION

The present invention addresses the above and other needs by providing a cochlear electrode design having a curved electrode array for insertion into a cochlear cavity and methods for manufacturing various aspects of the cochlear electrode of the present invention.

In one aspect of the invention, there is provided an improved stimulation lead for implanting into a body cavity. The lead comprises: a flexible carrier having a proximal end, a distal end, a medial side and a lateral side; a distal, pre-curved lead section having memory; a plurality of electrode contacts embedded at the distal end of the lead, which electrode contacts comprise an electrode array; a plurality of conductor wires embedded in the carrier, each conductor wire connected to at least one electrode contact; and a longitudinal, stylet insertion channel within the carrier extending into at least a part of the distal, pre-curved lead section.

The pre-curved section of the lead, which includes at least some of the electrode array, has memory because the electrode contacts and connected conductor wires which form an electrode contact assembly are pre-bent into the desired curvature before the flexible carrier is formed around the electrode contact assembly. Thus, not only is the carrier molded into a predetermined curved shape having memory, but the electrode contact assembly is also pre-bent into a desired curvature to cooperate with the molded carrier shape. The pre-curved lead section has an internal, elastic characteristic, whereby straightening the curved section exerts an elastic, contractive tension, tending to restore that section to its initial shape.

The present invention utilizes various components in the lead design to cooperate and to achieve a desired, high compliance in the curve section of the lead. Specifically, conventional conductor wires are typically straight wires or coiled wires. The conductor wires of choice, however, are zigzag wires because they are relatively compliant, offer fracture resistance to bending and can be compactly bundled. While straight wires can be compactly bundled, they are more susceptible to bending fractures than zigzag or coiled wires. Coil wires are not as easily bundled compactly as straight or zigzag conductor wires. Although zigzagged conductor wires are preferably used, it is emphasized that the lead design of the present invention can incorporate a variety of conductor wire configurations including straight and coil type wires.

The lead of the present invention includes a stylet insertion channel which is used during implantation of the lead to help guide the lead into a cavity. For example, in the case of a cochlear stimulating lead, an insertion stylet may be inserted into the insertion channel to facilitate the initial placement of the lead tip into the scala tympani. While the stylet insertion channel may be directly formed within the lead carrier itself, such a stylet insertion channel may not give optimal results because the compliant carrier material may have a surface texture that is too sticky to function well as a stylet channel wall. Accordingly, the lead of the present invention not only includes a stylet insertion channel, but a part of this channel may be made from a thin-wall tubing that is a different material than the carrier material. A particularly suitable tubing material is Teflon® or polytetrafluoroethylene (PTFE) polymer.

Use of a Teflon tubing in the lead serves two major purposes. First, the Teflon is much stiffer than carrier material which is generally silicone or polyurethane. Incorporating a Teflon tubing therefore provides added stiffness to that part of the lead. Second, the Teflon tubing makes inserting and withdrawing a stylet into and out of the stylet insertion channel much easier because Teflon is a harder material and exhibits less friction than silicone or polyurethane. As a consequence, Teflon also does not tear as easily as the carrier material.

As yet another embodiment of the lead of the present invention, an overmold can be attached over the opening of the stylet insertion channel to minimize fluid and bacteria from entering the stylet insertion channel. The overmold may be made from the same material as the lead carrier material, e.g., silicone or polyurethane. A slit in the overmold is placed to allow passage of the insertion stylet through the slit and into the stylet insertion channel. The slit must be sized and configured to permit the stylet to pass easily through the slit. After the stylet is withdrawn, the slit, being made of a compliant material, will self-seal to some extent, as it returns to its original conformation.

As a further embodiment of the stimulation lead of the present invention, the use of the slit may not always be sufficiently tight to keep out fluid and bacteria and hence two additional devices may be used for sealing the slit in the overmold. The first device is a pin plug that has a head and a tail pin, which tail pin may have a curvature. The pin plug may be inserted head first into the slit in the overmold to seal the slit through a compression/friction fit. After the head has been inserted into the slit, the tail pin may be left outside the overmold. A second device is a malleable ring that may be formed into the overmold and encircles the slit. After the lead has been implanted with the insertion stylet and the stylet withdrawn, the ring may be crushed around the slit to provide a compression seal.

The lead, in accordance with the present invention, can be made in at least two specific embodiments for cochlear stimulation. One lead can be made for medial placement in the human scala tympani, which is one duct in the cochlea. This embodiment of the lead has a pre-curved section that is spiral shaped. The distal curved part of this lead has a length, taper, and curvature such that after implantation, the electrode array is implanted approximately one spiral turn in the scala tympani duct. This lead also can include a stylet insertion channel that extends into the distal curved section of the lead and also part of the slightly curved (substantially straight) lead section. The stylet insertion channel can be partly comprised of a Teflon tubing. It is emphasized that the tubing specifically does not extend into the aggressively curved, distal part of the lead, because if that were so, this curved part would become unacceptably stiff and non-compliant. It is also emphasized that the stylet channel continues into the distal curved section of the lead, but this section of the channel is formed from the carrier material itself. The Teflon tubing forms only that part of the stylet insertion channel that is the substantially straight or slightly curved section of the lead where additional stiffness is desired. Thus, use of the Teflon tubing contributes advantageously to a lead having differential compliance along its length.

Another, second embodiment of the cochlear lead is suited for deep, lateral (outer) wall placement in the scala tympani. With this embodiment, the distal section of the lead is hooked shape. This hooked, curved portion is comparatively longer than the lead embodiment for medial placement, in order to allow the second lead embodiment to be implanted into the scala tympani between about 1 to 2 turns. Because of the hook shape, when the second embodiment of the lead is implanted, the lateral side of the lead contacts the lateral or outer wall of the scala tympani. Such lateral contact may facilitate the deeper, up to 2 turn, implantation of the electrode array.

As an additional feature of the second cochlear lead embodiment, the very tip of the tapered, curved hook may be constructed to be "super-flexible." The super-flexible tip is short enough such that only a subset of the electrode contacts are actually part of this super-flexible tip. The super-flexible tip is achieved by (a) making the thickness of the tip very thin relative to the other part of the curved hook and (b) by excluding any part of the stylet insertion channel within this tip, since including a channel would necessarily require too thick a carrier and prevent super-flexibility. The super-flexible tip permits the lead to easily conform to the curvature of the scala tympani as the lead tip is being inserted and also to apply light pressure to the lateral wall of the scala tympani in order to minimize injury to the wall during insertion of the electrode array.

In another aspect of the invention, a method of manufacturing a stimulating lead having a pre-curved tip is provided. This method comprises: (a) attaching a plurality of inert electrode contacts onto a chemically dissolvable strip substrate having a first, distal end and a second, proximal end; (b) coupling each electrode contact to a conductor wire to create an electrode array assembly; (c) attaching the first, distal end of substrate to a revolving dowel, which dowel is integrated into a mold and inside a cavity; (d) attaching the proximal, second end of the substrate to a restraint which applies tension to the electrode array assembly; (e) turning the dowel to create a predetermined curvature on the distal end of the electrode array assembly; (f) delivering a body-compatible carrier material into the cavity and around the electrode array assembly to create a carrier/covering; (g) releasing the formed lead from the mold; and (h) applying a weak acid and heat to the chemically active substrate to dissolve away the substrate and expose the inert, electrode contact on the surface of the lead. The method described can produce a lead with an electrode array having a curved tip with elastic, memory properties.

The process above may be modified to incorporate a stylet insertion channel in the body of the lead. This is accomplished by inserting between step (e) and (f), the step (e1): placing a mandrel into the cavity, oriented approximately parallel to the electrode array assembly, wherein the proximal end of the mandrel is situated to escape coverage by injected carrier material. Further, anytime after step (g), another step is added: (g1) pulling the mandrel out of the carrier to create a stylet insertion channel with a channel opening on the lead. In addition, after the mandrel is pulled out, the opening of the channel opening may be covered with an overmold having a slit opening therethrough to allow access into the stylet channel. This process can be used to produce a pre-curved lead having a stylet channel concurrently in the portion of the substantially straight or slightly curved section of the lead as well as the aggressively curved section of the lead.

As an alternative embodiment of the above method, the stylet channel may include a thin-wall Teflon tubing. This is accomplished by inserting between step (e) and (f) the steps: (e1) placing a mandrel inside the lumen of a thin-walled Teflon tubing; and (e2) placing the combination of the Teflon tubing with the inserted mandrel inside the tubing into the mold cavity, the combination oriented approximately parallel to the electrode array assembly, wherein the proximal end of the mandrel is situated to escape coverage by the delivered carrier material. Also any time after step (g), the following step can take place: (g1) pulling the mandrel out of the Teflon tubing to create the stylet insertion channel. While the mandrel may be made from various materials, one option is to use a mandrel that is made of Teflon. After the Teflon mandrel has been pulled out of the formed lead, leaving the Teflon tube incorporated into the lead, an overmold, which has a slit opening, may be attached over the opening of the stylet insertion channel. This latter embodiment produces a differentially compliant pre-curved lead by employing the Teflon® tubing as a stiffener.

The above-described manufacturing process can produce a pre-curved lead having a stylet channel extending from the curved, distal end to the substantially straight section of the lead. Again, it is emphasized that the Teflon tube comprises only a part of the total length of the stylet insertion channel.

That is, the tube occupies only the substantially straight or slightly curved lead section and not the distal, aggressively curved section.

The presence of the Teflon tubing is advantageous as it presents less friction and is more resistant to tears than the carrier material which is often silicone or polyurethane. An insertion stylet can be more easily inserted into and withdrawn from the Teflon tubing with the reduced possibility of a wall tear in the channel. A second important benefit provided by the Teflon tubing is that it provides differential stiffness to the lead. The distal, tapered, curved portion of the lead can be compliant and gentle while being inserted into the scala tympani, while the substantially straight section of the lead is made stiffer by the presence of the Teflon and thereby facilitates the directional placement of the lead near the target cochlea.

In another aspect of the present invention, a method is provided for implanting a stimulating electrode having an insertion stylet channel with a channel opening on the lead body. The method comprises: (a) implanting the lead using the stylet; (b) withdrawing the stylet from the lead; and (c) capping the insertion stylet channel opening. As described, the channel opening may be capped by attaching an overmold with a slit that is sized to permit through access for an insertion stylet. The slit may be subsequently sealed with a pin plug or with a malleable ring encircling the slit.

As yet another aspect of the present invention, a lead system is described comprising: a cochlear lead, a pin plug, and an insertion tool. The cochlear lead includes: a flexible carrier having a proximal end and a distal end; a stylet insertion channel incorporated into the flexible carrier; and an electrode array placed on the distal lead end. The pin plug for capping the insertion stylet has a head and tail pin with a curvature in the tail pin. The insertion tool has a first end and second end. The first end of the insertion tool has a pin plug holding channel that accommodates and holds the tail pin with a friction fit to help insert the head of the pin plug into the lead to cap the stylet insertion channel.

It is thus a feature of the present invention to provide a lead design having a pre-curved electrode array having an elastic characteristic which tends to restore the electrode array to its pre-curved shape after implantation.

It is another feature of the invention to provide specific embodiments of the lead which have compliant electrode arrays that are gentle to the walls of the scala tympani, whether the electrode array is intended to engage the medial or lateral wall of the scala tympani.

It is yet another feature of the invention to provide a differentially compliant lead having a stiff, substantially straight section and a more compliant distal, curved section.

It is a further feature of the invention to provide a lead having a stylet insertion channel and devices for sealing the opening of the stylet channel.

BRIEF DESCRIPTION OF THE DRAWINGS

The above and other aspects, features and advantages of the present invention will be more apparent from the following more particular description thereof, presented in conjunction with the following drawings wherein:

FIG. 2 shows, in accordance with the present invention, an illustration of another embodiment of the cochlear lead with an electrode array that is much longer and less curved and has a tip that is more tapered and designed for deeper, lateral placement in the cochlea (between about 1.5 to 2.0 turns in the cochlea) compared to the lead of FIG. 1;

FIG. 3A shows, in accordance with the present invention, a cross-sectional view of the lead of FIG. 2 at line 3A-3A;

FIG. 3B shows, in accordance with the present invention, a cross-sectional view of the lead of FIG. 2 at line 3B-3B;

FIG. 3C shows, in accordance with the present invention, a fragmentary view showing the exposed electrode contacts on the medial side of the lead of FIG. 2;

FIG. 3D shows, in accordance with the present invention, a partial view of zigzag conductor wires coupled to three electrode contacts;

FIG. 4 shows a partial, longitudinal, cross-sectional view of one embodiment of a lead of the present invention, omitting the conducting wires, but showing an integrated Teflon tubing that forms a part of the stylet insertion channel and an overmold that caps the end opening of the stylet insertion channel;

FIG. 7A shows, in accordance with the present invention, a pin plug that caps an overmold slit opening into a stylet channel and a pin plug insertion tool for holding the pin plug while it is inserted into the overmold slit;

FIG. 7B shows, in accordance with the present invention, an alternative device for sealing the overmold slit, which device is a malleable, cylindrical ring installed around the overmold slit and which ring can be crushed to compressively seal the overmold slit and hence the stylet insertion channel;

FIG. 9A shows a close-up view of a zigzag conductor wire that may be used in the cochlear electrode of the present invention;

FIG. 9B shows, in accordance with the present invention, a view of the zigzag wire conductor forming apparatus comprised of two wheels (or gears or cylinders) having complementary teeth, which apparatus can be used to quickly manufacture the zigzag conductor wire;

FIG. 11 shows, in accordance with the present invention, a view of a molding apparatus for forming a polymer carrier, e.g., silicone or polyurethane that covers an electrode array assembly;

FIG. 12 shows, in accordance with the present invention, another view of the curved, electrode assembly and the molding apparatus of FIG. 11;

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The cochlear electrode of the present invention may be used with an implantable multi-channel pulse generator, e.g., an implantable cochlear stimulator (ICS) of the type disclosed in U.S. Pat. No. 5,603,726, incorporated herein by reference in its entirety or with other suitable stimulators. It is to be understood, however, that although a cochlear lead is used as an exemplary context, the lead of the present invention, including the method of manufacturing, may be applied to other medical applications.

Figure 1:
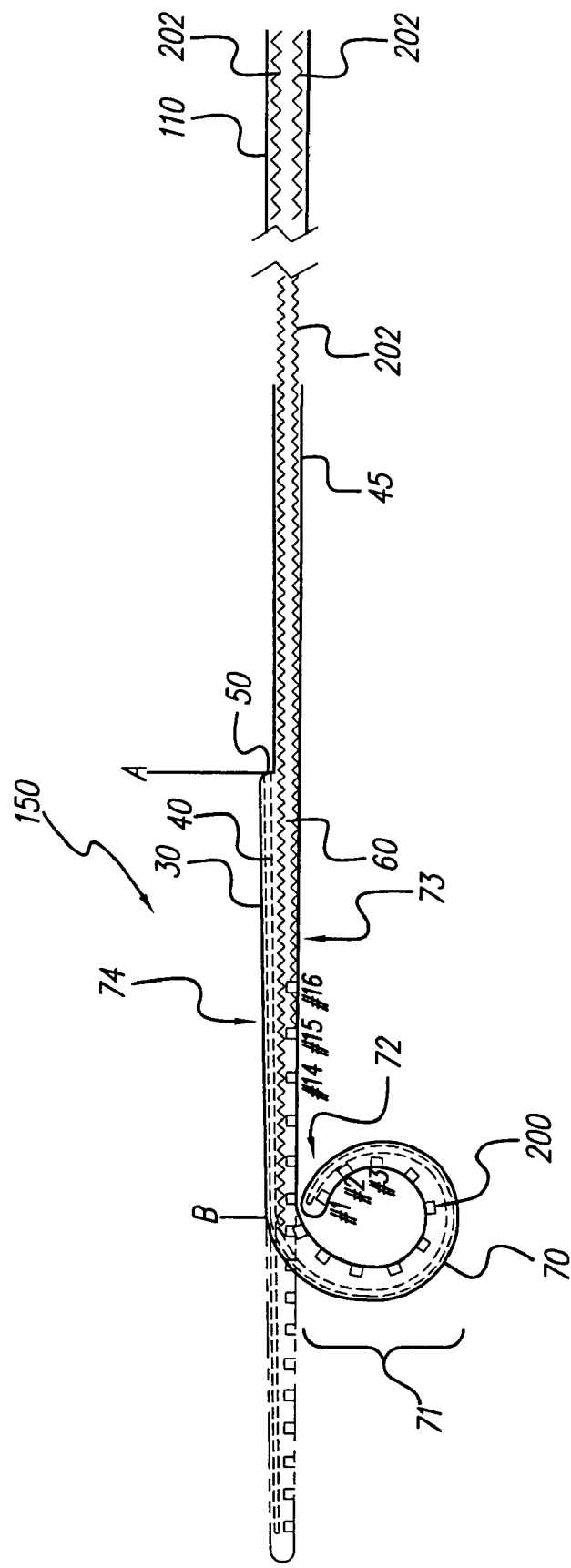
FIG. 1 shows, in accordance with the present invention, an illustration of one embodiment of the cochlear lead with an electrode array having about a 360° spiral curvature for perimodiolar placement.

FIG. 1 shows one embodiment of the lead 150 made in accordance with the present invention. In a cochlear application, the lead 150 has an outer (lateral) surface 74 for contacting a lateral wall in scala tympani, a medial surface 73 which is opposite the lateral surface 74, and a distal tip 72. The lead has approximately a 360° curvature at the distally located electrode array 70 and is intended to be implanted in the cochlea with a turn of between about 360° to 400° (or about one full turn). The lead is comprised of an electrode array 70 that has a plurality of spaced-apart electrode contacts 200, a middle section 30 shown as between point A to point B in FIG. 1, which middle section may be substantially straight or slightly curved. This middle section 30 which is referred to as the "substantially straight section" shall include all lead embodiments that are in fact straight, as well as those leads which are slightly curved in section 30. It can be seen that the substantially straight section 30, can overlap a part of the electrode array 70 which array also encompasses the distal curved part of the lead 71. A thin section 45 of the lead, shown in FIG. 1 as right of point A on the lead and a thicker, more proximal lead portion 110 carries a plurality of conductor wires 202 for connection to an implantable, multi-channel stimulator or to an ICS which can be inductively powered through the skin. The thin, lead section 45 is thinner than the substantially straight or slightly curved section 30 which is necessarily thicker to accommodate the stylet insertion channel 40. The distal curved part 71 of the lead 150, which includes the electrode array 70, straightens when a stylet is inserted into the stylet channel 40. As the stylet is withdrawn, the curved parts of the lead, being formed from a material having memory, tends to returns to its original curved position.

Some representative dimensions of this lead 150 can be as follows. The substantially straight section 30 can be about 15 millimeters long. This substantially straight section 30 combined with the curved electrode array portion 70 which partially overlaps, may be about 25 millimeters long. The width of the electrode array section 70 may be about 3.0 millimeters in diameter plus or minus 0.5 millimeters. Proximal lead portion 110 is connected to the thin lead section 45 and may be variable in length.

The profile of the lead 150 along its length can vary, as shown in FIG. 1. For example, electrode array 70, in addition to being aggressively curved, can be gently tapered towards the distal end of the lead 150. Such tapering accommodates the natural, tapered shape of the scala tympani wherein the electrode array 70 is to be inserted. The lead 150 has a stylet insertion channel 40 and may have a channel opening 50. The channel 40 extends through the substantially straight section 30 of the lead 150 and proceeds further into the aggressively curved part of the lead which is part of the electrode array 70.

The plurality of conductor wires 202 are coupled to the electrode contacts 200 in the electrode array 70 and these conductor wires extend through the lead to the proximal lead portion 110 and may be terminated in a proximal connector (not shown). The embodiment of the electrode array 70 shown has sixteen electrode contacts 200, each numbered from #1 to #16. Electrode contacts numbered #10 through #16 are within the substantially straight (or slightly curved) section 30 of the lead, while the electrode contacts #1 through #9 are within the aggressively curved section of the lead.

The insulative covering/carrier 60 which forms the body of the lead and provides a covering over the conductor wires 202 can be made from silicone, polyurethanes or other body-compatible, polymeric insulating materials. The type and hardness of the insulative carrier 60 can be selected to provide a specific, desired compliance to the lead body in combination with the compliance of the conductor wires and choice of structures incorporated into the lead 150, e.g., the stylet insertion channel 40.

An important aspect of the present invention which determines the lead's mechanical characteristic is that the carrier/covering material is molded to assume a specific pre-curved shape having memory. Therefore, the natural resting position of the lead has a curved, distal lead tip. When the distal tip is straightened by inserting a relatively stiff stylet into the stylet insertion channel 40, the carrier/covering 60 in the distal curved tip as well as the slightly curved section 30 of the lead 150 stores elastic energy which exerts a contractive force tending to restore the lead to its originally molded curved shape. The lead embodiment in FIG. 1 shows a spiral curve at the tip of the lead, which tip completes a 360° circular loop. When such a lead is implanted, the medial side of the lead having the electrode contacts 200 hugs the modiolar wall and thus achieves a medial electrode array placement.

FIG. 2 shows an alternative embodiment of a lead 150', made in accordance with the present invention, which is similar in construction to the lead 150 depicted in FIG. 1, except with respect to the degree of curvature of the distal portion of the lead and the length of the curved electrode array which can be up to two and half times longer for the lead shown in FIG. 2. The lead in FIG. 2 assumes a hooked shaped and has a curvature which is less aggressive than compared to the lead depicted in FIG. 1. The lead embodiment of FIG. 2 is used for deep, lateral implantation of the electrode array into the cochlea. The lateral side of the lead 150' is that side opposite to where the electrode contacts 200 are located.

The electrode array, when implanted, may turn inside the cochlea from between about 1.5 to about 2.0 turns. The distal lead tip which has electrode contacts #1 to #5 is very narrow and tapered. This particular tapered shape accommodates the tight curvature and narrower passageway proceeding into the duct of the scala tympani, particularly in the second turn. In addition, the tapered lead tip containing electrode contacts #1 to #5 is "super-flexible", in part, owing to the thinness of the tip and, moreover, by selecting an extremely compliant carrier material and further by utilizing a compliant, zigzag conductor wire. The overall curvature of the electrode array in FIG. 2 is more gradual than the one depicted in FIG. 1.

In use, the electrode array shown in FIG. 2, will tend to abut against the outer (lateral) wall in the scala tympani while being inserted. The contact pressure with lead 150' is also between the lead and the lateral wall, unlike lead 150, which contacts the medial wall in the scala tympani. While such lateral lead contact is generally less efficient for stimulation because it places the electrode contacts further away from the target ganglion nerves, this mode of placement and degree of electrode array curvature may be advantageous when implanting the electrode array deeply into the cochlea for more than 1.5 turns, since a more aggressive curvature, such as used in the lead 150 shown in FIG. 1, can cause undesirable sticking or jamming in the second turn of the cochlea when combined with an increased length to the electrode array.

Referring to both FIGS. 1 and 2, the electrode contacts 200 are spaced apart along the medial side of the lead, which side is on the inside of the curvature of the curved electrode array. In the lead embodiments shown, the electrode arrays are positioned as "in-line" electrodes, meaning that they are spaced apart more or less in alignment with the lead axis. To have an in-line configuration of electrodes, a perfectly straight alignment is not necessary. Rather, "in-line" shall mean, as used herein, two or more electrodes placed on a linear lead, one electrode placed more distal to another electrode.

FIG. 3A depicts a cross-sectional view at line 3A-3A of the lead in FIG. 2, showing the insulation coated conductor wires 202 within the triangular-shaped electrode contact 200. The triangular-shaped electrode contact 200 is comprised of two folded strips 220 and 210. The insulation coated conductor wires 202 may be enclosed in a triangle shape when strip 220 is folded. Alternatively, the strips may be folded upwards into a "U" shape. Note that there is no stylet channel in this view since the channel 40 does not extend this far into this distal, super-flexible tip of the lead.

FIG. 3B shows a cross-sectional view at line 3B-3B of the lead in FIG. 2, showing the stylet insertion channel 40 within the carrier/covering 60 and the conductor wires 202 within the triangular-shaped electrode contact 200. The triangular-shaped electrode contact 200 is comprised of two folded strips 220 and 210. The channel 40 may be coated with a slippery material to facilitate the insertion and withdrawal of a stylet. Alternatively, in one preferred embodiment, the insertion channel 40 may be formed from a tube 41 which presents its own wall, as shown in FIG. 3B.

As further shown in FIG. 3B, the inside surface of the triangular electrode 200 may be coated with an insulation coating 205 which prevents the possibility of shorting through an inadvertent exposure of the insulation of a conductor wire 202. The conductor wires 202 are insulated with a material such as parylene or Teflon® coating. In the event that the insulation is scraped off from the conductor wire, the presence of the inner coating 205 can prevent a short to the electrode 200. While the cross-sectional view of FIG. 3B is taken with respect to FIG. 2, it will be appreciated that this same view applies equally to cross-sections of the lead in FIG. 1 taken at approximately the same locations.

FIG. 3C is a fragmentary, medial view of an electrode array 70 of the lead shown in FIG. 2 showing an example inter-contact spacing for the electrode contacts 200 exposed on the surface of the lead carrier. The electrode contacts 200 can have a surface area having dimensions of about 0.50 by 0.40 millimeters and the inter-contact spacing can be about 1.20 millimeters.

FIG. 3D shows, in accordance with the present invention, an electrode array assembly 79 with a view of the conductor wires 202', 202" and 202''', which are zigzagged in shape in one embodiment of the lead. The electrode contacts shown are #1, #2 and #3. Zigzagged conductor wire 202' is connected to the electrode contact #3 electrode while conductor 202" and 202''' run past electrode contact #3 through the triangular electrode assembly. Next, conductor wire 202" is connected to electrode contact #2 and conductor wire 202''' is run through the triangular electrode assembly of electrode contact #2. Finally, the last conductor 202''' is attached to the last and most distal electrode contact #1. The basic connection sequence shown for electrode contacts #1, #2 and #3 is followed for the remaining electrode contacts #4 through #16 which are not shown in FIG. 3D.

The zigzagged conductor wires described resist bending fractures better than a straight conductor wire. At the same time, in combination with a soft, compliant carrier/covering, the zigzagged wires permit the lead to exhibit higher compliance compared to a lead using other conductor configurations such as coils or straight conductor wires. This higher compliance advantageously allows the curved electrode array 70, as shown in FIG. 2, and particularly the superflexible tip 260 to be very compliant while the electrode array is being implanted into the cochlea and, thus, to be very gentle to the cochlear walls. Furthermore, because of this higher compliance, the electrode array does not place undue pressure on the walls of the cochlea while the array is chronically implanted, thereby averting even the remote possibility of wall damage after implantation.

FIG. 4 shows, in accordance with the present invention, one embodiment of the lead 150 showing a partial, longitudinal, cross-sectional view. This view omits showing the conductor wires and the proximal end of the lead. The stylet channel 40 is partly formed by placing a Teflon® (or PTFE) tubing 41 into the slightly curved section 30 (between points A and B) of the lead 150. It is emphasized, however, that beyond point B, the stylet channel section 52 is formed by the carrier material itself, such as silicone or polyurethane since the curved tip must be flexible and the Teflon would add undesirable stiffness to the tip. The Teflon tubing 41 provides a separate wall which is more abrasion and tear resistant than the surrounding material of the insulative carrier. The Teflon surface also tends to be smoother and presents less friction to an inserted stylet than the insulation carrier. The stylet channel 40 formed partly by the Teflon tubing 41 therefore facilitates the easy insertion of the stylet into the channel and removal when the stylet is no longer needed. A stickier material such as silicone, however, can cause binding between the stylet and the lead and increase the chance for dislodging the lead from its desired location.

The Teflon tubing 41 provides a second important advantage: it provides added stiffness to the lead 150 to maintain the substantially straight or slightly curved section 30 from buckling during insertion of the electrode array section 70 into the cochlea. The tapered, curved portion of the electrode array which is not stiffened by the Teflon tube, however, remains desirably compliant as the insertion stylet is inserted into the stylet channel and as the electrode array is pushed off the stylet. The substantially straight (or slightly curved) section 30 of the lead is advantageously more stiff, since it needs to remain straight during implantation. Because it does not enter the cochlea, the substantially straight section 30 does not need to be as compliant as the highly curved section of the lead. The Teflon tubing 41 thereby advantageously provides a differential compliance for the different sections of the lead 150.

Figure 5:
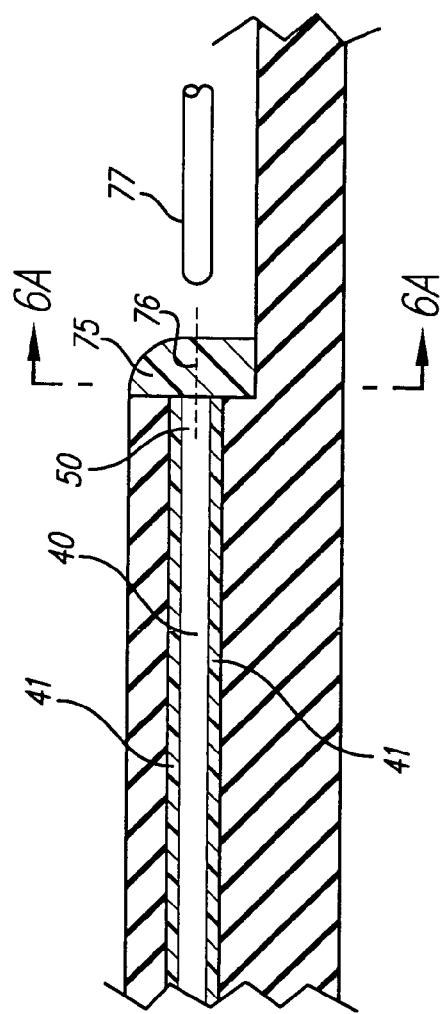
FIG. 5 shows, in accordance with the present invention, another longitudinal, cross-sectional view of the overmold and part of the cochlear lead shown in FIG. 4.

FIGS. 4 and 5 show, in accordance with the present invention, an overmold 75 which may be used to cover the end opening 50 of the stylet insertion channel 40. It is noted that FIGS. 4 and 5 omit showing the conductor wires for purposes of simplicity. The overmold 75 can be made from an implantable grade silicone, polyurethane or other polymer material and can have a puncture or a slit 76 therethrough, as shown in FIG. 5. FIG. 5 also shows a Teflon tubing 41 incorporated into the lead in conjunction with the overmold 75. The Teflon tubing 41 can form the stylet channel 40 and the tubing or channel opening 50 can abut the overmold 75 as shown. A tip of an insertion stylet 77 can be inserted through the slit 76 and into the stylet insertion channel 40 when the electrode array is being implanted. After implantation, the stylet 77 is withdrawn from the insertion channel 40 and the slit 76 in the overmold 75, being made of compliant material, will tend to return to its original state, closing the slit.

Figure 6:
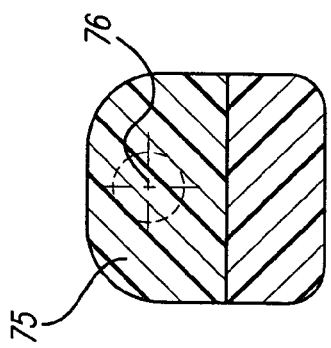
FIG. 6 is, in accordance with the present invention, a cross-sectional view of the overmold and the cochlear lead shown in FIG. 5 along lines 6A-6A, showing a cross-configured slit in the overmold.

FIG. 6 shows, in accordance with the present invention, a cross-sectional view of the overmold and part of the lead at line 6A-6A of FIG. 5. For simplicity, the conductor wires running through the lead are not shown in FIG. 6. While a cross-configured slit 76 is depicted here, it can be appreciated that other configurations of punctures or slits can be used with equal effect.

The slitted overmold 75 helps to keep unwanted bacteria from entering the stylet channel after the lead/electrode array has been implanted. If the stylet channel opening 50 is not covered, there is an increased chance that the stylet insertion channel 40 may become a site for bacterial growth, particularly since the open stylet channel may easily allow entry of bacteria but cannot be reached by the body's cellular, immune defense, i.e., white cells. There is a remote possibility that bacteria that has grown in the stylet channel will escape into the cochlea through small pores or fissures in the wall of the carrier/covering. The use of an overmold to seal the opening of the stylet channel can help forestall this occurrence.

FIG. 7A-C illustrate, in accordance with the present invention, two devices that may be used to further cap the slitted overmold shown in FIG. 5 after the insertion stylet has been removed. FIG. 7A shows a pin plug 95 having a circular head 93 and a tail pin 94 having a curvature 90 in the middle of the pin. To help insert the pin plug 95 into the overmold 75, a pin plug insertion tool 97 may be used. The elongate insertion tool 97 has a first end 98 and a second end 99 and has a small channel 92 on the first end 98. The tail pin 94 of the pin plug 95 can be inserted into the small channel 92 which has a diameter that is sized to accept the tail pin and hold it tightly in a friction/compression fit. The exterior diameter of the first end of the insertion tool 97 may be about the same diameter or smaller than the pin plug head 93. As such, the pin plug head 93 and the first end 98 of the insertion tool 97 may be inserted head first through the cross slit 76 shown in FIG. 6 and inserted into the compliant overmold 75 such that the pin plug head 93 is abutted against the tubing end 51 to help seal the channel 40. As the insertion tool 97 is withdrawn from the overmold 75, the pin plug 95, which is compressed and grabbed by the compliant overmold 75, will remain in place within the overmold. The tail 94 may be left protruding from the overmold 75 without concern. This tail 94 may be grasped at some later time to retract the pin plug 95 from the overmold 75, if necessary.

FIG. 7A also depicts an embodiment of the lead in which a Teflon tubing 41 forms the stylet channel 40. In such a case an overmold 75 may also be employed. The Teflon tubing end 51 is placed abutted to the overmold 75. The thickness of the overmold may be, for instance, about 1.0 millimeter. As other example dimensions, the stylet channel 40 can have an inner diameter of 0.30 millimeters and the diameter of the pin plug head 93 can be 0.40 millimeters. The pin plug 95 can be made of, in one embodiment, body compatible polymer or non-corroding metals such as platinum, platinum/iridium alloy or gold or a combination thereof.

As shown in FIG. 7B, another method for capping the tubing end 51 is to employ a small, malleable, ring 43 implanted at the opening of the stylet channel 40. A Teflon tubing 41 may be used to form the stylet insertion channel 40. There is no separate overmold in the example lead shown in FIG. 7B. The ring 43 may be made of a body compatible, malleable metal. The slit 76 in the carrier insulation can be closed by crushing the ring 43 around the slit.

FIGS. 8A through 8D illustrate one method of making the electrode array assembly 79 of the present invention. To illustrate the process of assembling the electrode contacts and the conductive wires, the process will be described relative to the fabrication of an electrode array suitable for insertion into the cochlea. It should be emphasized that the method of making the electrode array depicted in these figures is not the only way to make lead 150 and electrode array 70. However, it represents one way to easily and inexpensively make the leads and electrode arrays depicted in FIGS. 1 and 2.

Most designs of cochlear leads and connectors are made by forming a polymer carrier such as silicone or polyurethane over an assembly of electrode contacts 200. The electrode contacts 200 which actually make contact with the stimulated tissue are generally made from a biocompatible, electrically conductive material such as an electrically conductive, relatively inert metal, e.g., platinum or a platinum/iridium alloy. The electrode contacts 200 are located in a controlled position in reference to the surface of the lead carrier, with a specified surface portion of the electrode contact left exposed for contacting the body tissue to be stimulated. Disadvantageously, making such electrode arrays can be extremely difficult, especially when the electrode contacts are very small and when a large number of electrode contacts are used, as is the case with a cochlear lead. One problem encountered in the fabrication of such electrodes is reliably holding the array of electrode contacts in the desired and stable position when welding the conductive wires to the contacts and when molding the carrier over the conductive wires. A further problem is to ensure that the portion of the electrode contact surface which is to be exposed is not covered by the carrier when the lead is molded.

As provided in FIGS. 8A through 8D, one method of making the electrode array of the present invention employs the principle of attaching electrode contacts 200 onto a chemically dissolvable, non-toxic, foil substrate 100, such as iron (Fe). The electrode contacts 200 can be made from precious, relatively non-reactive materials, e.g., platinum and its alloys, such as platinum/iridium. The electrode contacts can be resistance welded to the foil substrate 100. Resistance welding advantageously provides a secure attachment of the electrode contact material to the foil substrate 100 without causing a deep fusion attachment of the two materials. The resulting shallow fusion yields a clean, exposed electrode surface area to be formed when the foil carrier is later chemically etched away. Other types of attachment that result in shallow fusion between the electrode material and the foil substrate may be used in lieu of resistance welding.

Attached to the metal foil substrate 100, the electrode contacts 200 remain in a desired and stable position allowing the conductor wires 202 to be easily connected to the contacts 200 and, subsequently, allowing the insulative polymer carrier to be molded over the conductor wires 202. After the molding process is completed, the metal foil is chemically etched away using a mixture of diluted acids, such as $HNO_3$ or HCl, heated to 90° Celsius. The electrode contacts and polymer carrier are largely inert to the acid and hence remain unaffected.

Figure 8A:
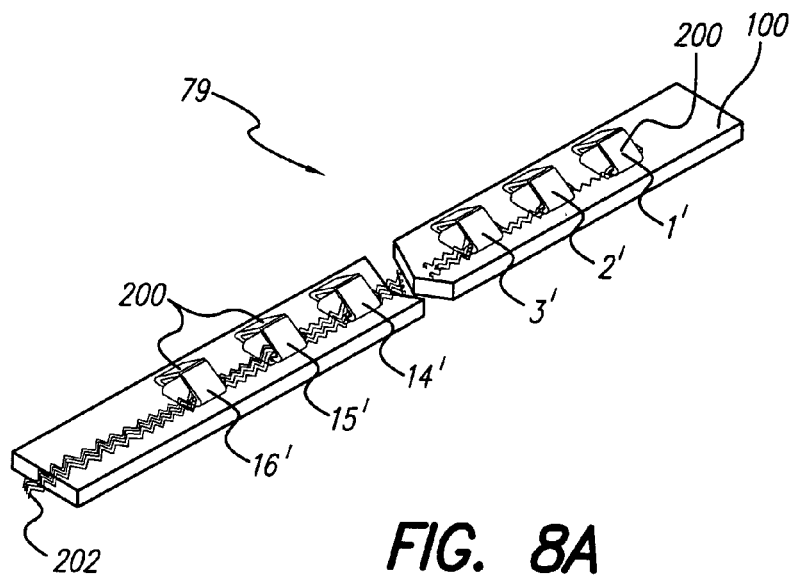
FIGS. 8A through 8D depict various views of the manufacturing process for assembling the electrode array of the present invention and coupling the conductor wires to the plurality of electrode contacts.

FIG. 8A illustrates an electrode array assembly 79 comprised of electrode contacts 200 which are resistance welded onto an Fe substrate 100 assuming an in-line, spaced-apart configuration. One conductor wire 202 can be uniquely coupled to the electrode contacts 200 that are numbered #1-16. For simplicity, only six of the sixteen electrode contacts used in the electrode array 70 are shown in FIG. 8A. Typically, a conductor wire 202 will connect to one of the electrode contacts 200 and another conductor wire from bundle 203 will connect to another electrode contact 200 and so on.

Figure 8B:
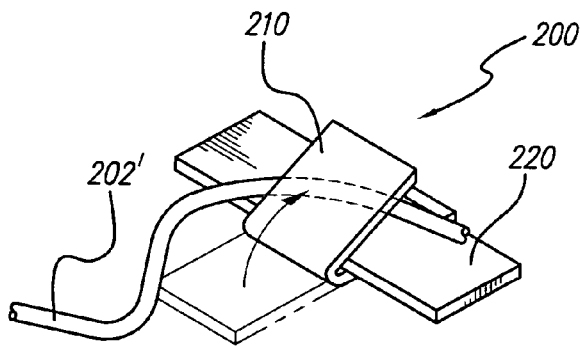

FIG. 8B shows that each electrode contact 200 consists of two pieces of platinum strips 210 and 220 connected together and joined to the iron foil 100 (FIG. 8A) by a shallow-fusion spot weld. These strips are initially arranged to form a "T" shape, viewed from the top, with the strip 210 forming the leg of the "T" and the strip 220 forming the cross bar of the "T". The legs of each "T" are arranged in-line, with proper spacing therebetween.

As seen in FIG. 8B, an insulated conductor wire 202' is laid on top of the electrode foil strip 220. The leg of the "T", which is the foil strip 210, is then folded over to hold the end of the conductor wire 202' while it is welded in position. The weld, preferably a resistance weld, burns away any insulation from the tip of the conductor wire 202' and makes a secure mechanical and electrical connection between the wire 202' and the electrode contact 200.

Figure 8C:
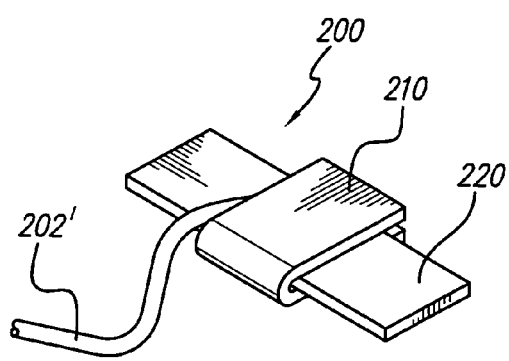
Figure 8D:
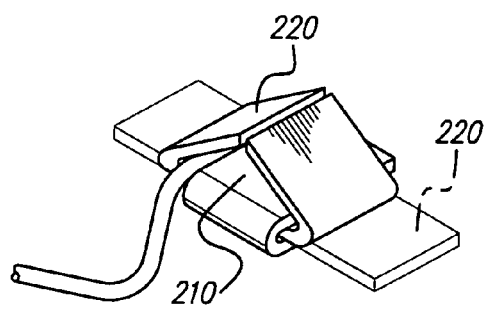

FIG. 8C shows the result of an electrode contact 200 having a wire 202' securely attached thereto. If other conductor wires are present, e.g., going to more distal electrode contacts, then such wires can pass over the foil piece 210 to form a bundle of conductor wires. The end flaps of the strip 220 may then be folded upwards to form, in a one embodiment, a triangular shape, as depicted in FIG. 8D. Alternatively, the end flaps of the strip 220 may be folded into an open "U" or staple shape, instead of a triangular shape.

While FIGS. 8A-D show zigzagged wire conductors 202, straight conductors may be used for some cochlear applications. Nevertheless, when high lead compliance is desired, a zigzag conductor wire 202 shown previously in FIG. 3D, is preferable. The method of assembling the conductor wires and coupling them to the electrode contacts 200, however, is essentially identical to the process described above for FIGS. 8A-D whether the conductor wires are zigzagged or straight.

FIG. 9A depicts, in accordance with the present invention, one strand of a zigzag conductor wire 202 showing one set of conductor wire dimensions used in a cochlear stimulation lead. The conductor wire 202 can have a diameter of about 0.025 millimeters, a trough-to-peak width of 0.20 millimeters and, R, the radius of curvature 56 of a peak (or a trough) of 0.05 millimeters, and a single bend of approximately 90° between adjacent wire segments 57 and 58.

FIG. 9B illustrates, in accordance with the present invention, an apparatus 85 used for manufacturing a zigzag conductor 202 wherein two toothed wheels (or cylinders) 80 and 81, respectively, are employed. The first wheel 80 has teeth 82 and the second wheel (or cylinder) 81 has complementary teeth 83. It can be seen that the teeth 82 and complementary teeth 83 can be shaped in many configurations, including that which yields the zigzag wire shape shown in FIG. 9A. One strand of straight wire 204 may be fed into the rotating wheel apparatus 85 to produce one strand of zigzagged conductor wire 202. Alternatively, multiple strands of straight conductor wire 204 may be drawn between the two rotating wheels simultaneously to manufacture multiple strands of zigzagged conductors 202. The first wheel 80 and second wheel 81 are placed in a zigzag wire forming apparatus with a clearance between the two wheels to bend straight wire into zigzag wire. The clearance should be sufficient to allow the conductor wire or wires to pass without becoming crushed and pinched while forming the zigzag wire shape.

Figure 9C:
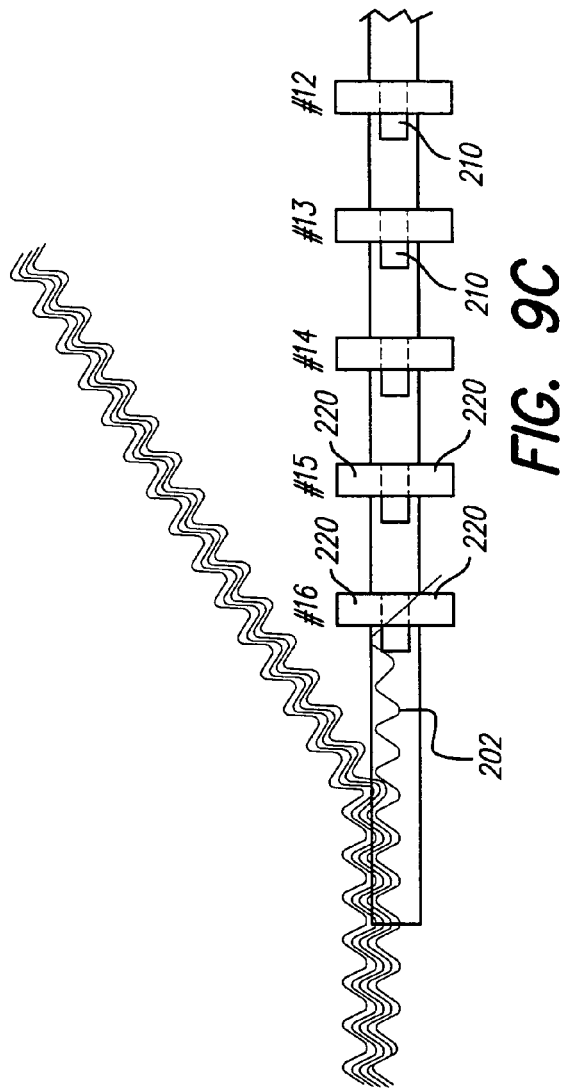
FIG. 9C shows, in accordance with the present invention, a view of an in-line electrode array assembly showing the foil strips in a "T" configuration before the foil strips are folded.

FIG. 9C shows a close-up view of how one strand of zigzagged conductor wire 202 is connected to electrode contact #16. Another wire strand is coupled to electrode contact #15 and so on until the last wire strand is connected to electrode contact #1. Then, the two flaps of strip 220 are folded upwards into a U shape or an enclosing triangle, while the bundles of conductor wires 202 are within the space between the flaps.

Figure 9E:
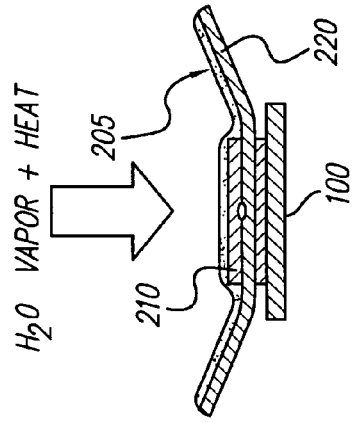
FIG. 9E shows, in accordance with the present invention, a cross-sectional view of the electrode assembly of FIG. 9D showing the layer of polymer over the top surface before the flaps of the top of the "T" are folded over.
Figure 9D:
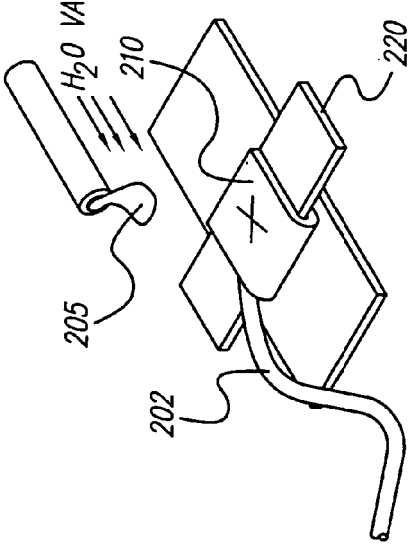
FIG. 9D shows, in accordance with the present invention, an illustration of a heat cured polymer being applied to a surface of a folded leg of the "T" indicated by an "X" and to the top flap of the "T."

FIGS. 9D and 9E illustrate, in accordance with the present invention, a preferred embodiment for manufacturing the electrode array by placing an insulation covering on the inside of the triangular-shaped electrode contact. After a conductor wire 202 has been welded to the electrode contact, a coating of insulation 205 is applied to the inside surface of foil 210 of the electrode contact 200 to provide a precautionary insulative barrier in the unlikely event that one of the passing wire conductors 202 should have an inadvertent exposure in the insulation covering. While there are many types of insulation material that may be applied, a preferred material is a polymer 205, as shown in FIG. 9D, that may be quickly cured with an application of heat and water vapor. Alternatively, the polymer 205 may be cured by applying a dose of ultraviolet radiation to a UV sensitive polymer.

Figure 10:
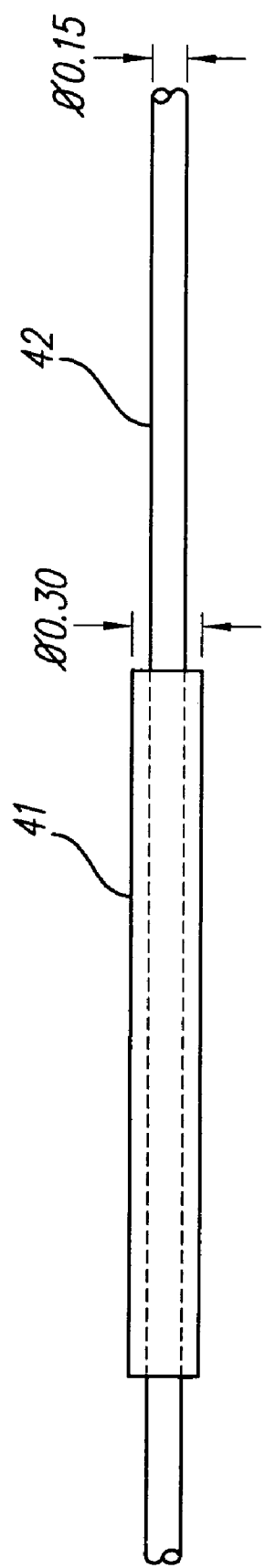
FIG. 10 shows, in accordance with the present invention, a view of a thin mandrel inserted within the lumen of a Teflon tubing, which Teflon tubing can be part of the lead shown in FIGS. 4, 5, 7A or 7B.

FIG. 10 shows, in accordance with the present invention, a small diameter, Teflon mandrel 42 inserted into a thin-walled, Teflon tubing 41. This mandrel 42 is employed to make a lead which has a Teflon tubing 41 forming the stylet insertion channel 40, as shown in FIG. 4. During molding of the carrier/covering 60 of lead 150, the mandrel 42 is inserted into the channel of tubing 41. After the carrier/covering is molded over the completed electrode assembly with the conductor wires connected, the mandrel 42 is withdrawn leaving the Teflon tubing 41 inside the lead carrier/covering and forming a stylet channel 40 within the lead.

FIGS. 11 and 12 show, in accordance with the present invention, a die and rod apparatus for molding the carrier over the conductive wires 202 and electrode contacts 200 that are pre-welded to an Fe substrate 100. One end 108 of the Fe substrate is fixed to a revolving dowel 104 which can be rotated to curve the Fe substrate and electrode array assembly 103. To create a lead shown in FIG. 1, the dowel 104 is rotated 360° to create the circular loop, as shown in FIG. 12. The other end 109 of the Fe substrate 100 is fixed to an attachment and restraint device 102 which keeps the substrate under continuous tension while the dowel 104 is rotated. After the circular loop is created at the distal part of the electrode array assembly, silicone is injected into the cavity 115 of the mold 105 which can be comprised of at least two detachable pieces 106 and 107.

Figure 13:
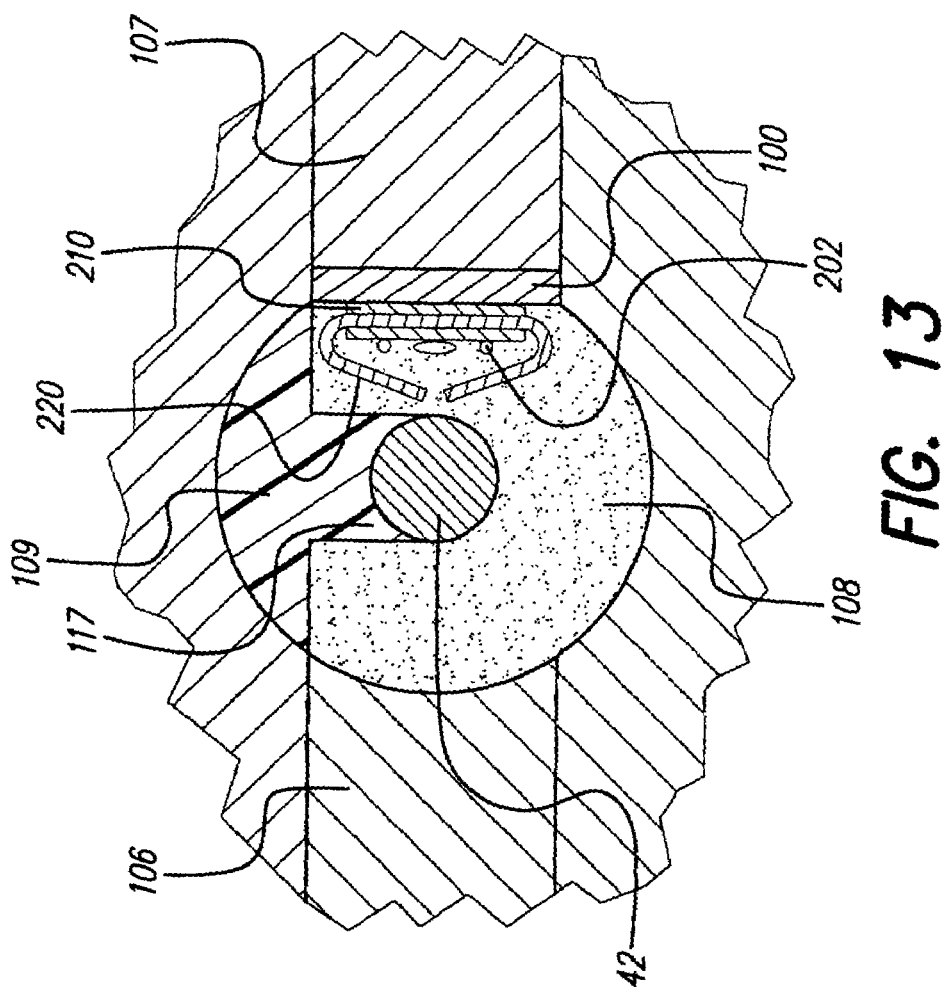
FIG. 13 shows, in accordance with the present invention, a cross-sectional view of the mold for forming the carrier/covering over the electrode array assembly.

FIG. 13 shows, in accordance with the present invention, a cross-sectional view of the die and electrode as shown in line 13A-13A of FIG. 11. In the first molding pass the U-shaped, carrier portion 108 is created by placing a first complementary die (not shown) over the top of the open die portions 107 and 106 and injecting a carrier polymer into the formed cavity 115, which cavity is shaped as the exterior of curved section of the lead. In the second molding pass, the first complementary die is removed and a Teflon mandrel 42 is inserted into the U-shaped trough 117. A second complementary die (not shown) is placed over the open die portions 106 and 107 and then silicone is injected into the remaining formed cavity and carrier portion 109 is formed which melds seamlessly with carrier portion 108. All die sections, including the second complementary die and die pieces 106 and 107, are disassembled and the lead assembly with the formed carrier/covering is freed from the mold. Then, the mandrel 42 is pulled out through stylet channel opening 50 creating the stylet channel 40. A separate overmold may be attached over the stylet channel opening 50. At some point after the lead has been released from the mold, weak heated acid is applied to dissolve the Fe substrate 100, which is no longer needed to hold the electrode contacts 200, thereby exposing the electrode contacts 200 on the surface of the lead.

If a Teflon tubing is desired as part of the stylet insertion channel, the combination of the Teflon tubing 41 with a Teflon mandrel 42 inserted within the tubing 41 is used, as shown in FIG. 10. This combination is then implanted into the trough 117 of carrier 108 instead of the Teflon mandrel 42 alone. The Teflon tubing should be positioned in the die 106 and 107 so that it is placed in the substantially straight or slightly curved portion 30 of the lead 150 or 150' such that, after being molded into the carrier, the Teflon tubing 41 will contribute to lead insertion stiffness and provide a slippery channel 40 for the insertion stylet. After the carrier/covering 108 and 109 are molded over the electrode/conductor wire assembly 103, the Teflon mandrel 42 is withdrawn, leaving the Teflon tubing 41 intact within the lead 150 or 150', and which Teflon tubing forms the stylet insertion channel 40.

Figure 14:
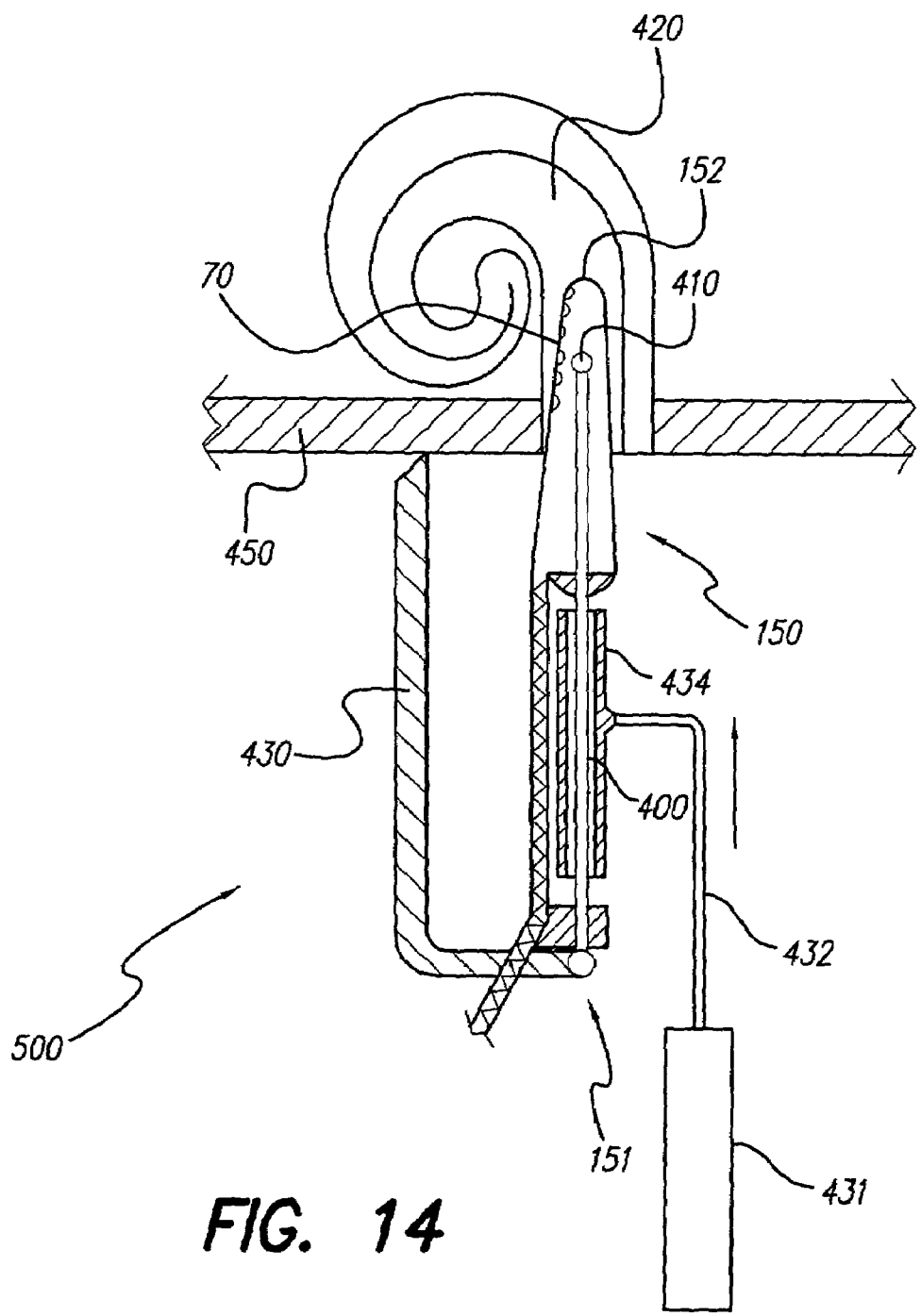
FIG. 14 shows an apparatus for implanting the electrode array of the present invention into a chamber of the cochlea.

FIG. 14 shows an apparatus 500 for gently implanting a pre-curved cochlear electrode array 70 as exemplified in FIGS. 1 and 2. To use this implanting apparatus 500 the lead must have a stylet insertion channel 40 since the apparatus 500 employs an insertion stylet 400 with a rounded tip 410. As noted previously, inserting the stylet 400 straightens a pre-curved lead 150 or 150' so that it may be initially inserted into the scala tympani 420. After the distal end of the arm 430 is abutted against the bone 450, the implanting apparatus 500 uses the stylet 400 as a guide and the sleeved part 434 is pushed using handle 431. A handle 431 is attached via arm 432 which is, in turn, connected to the sleeved part 434. The lead 150 is pushed off the stylet and, at the same time, the distal lead tip 152 is gently pushed into the curvature of the scala tympani 420, while the insertion stylet is maintained in a fixed position. The electrode array 70 of the lead 150 is radially oriented during insertion relative to the cochlea so that the electrode array 70 of the lead 150 can return to its original molded curvature within the scala tympani. Because of this tendency to return to the original curved shape, the tip 152 of the lead will follow a spiral pathway as the electrode array 70 is gently pushed off the stylet and into the cochlea.

The insertion apparatus arm 430 abuts against bone 450 hence limiting the depth of initial insertion of the electrode array and stylet tip 410 into the cochlea and thereby avoiding possible injury to the wall of the scala tympani. It can be seen with this particular implantation method that insertion and retraction of the stylet can be greatly facilitated by employing an insertion channel formed by an integrated Teflon tubing, since such a channel will exhibit superior abrasion resistance and low friction. In addition, the added stiffness provided by the Teflon tubing facilitates the initial placement of the lead 150 or 150' at the entrance of the scala tympani 420.

The lead design disclosed in FIG. 1 is a perimodiolar design for medial contact and which lead design has a curvature that places the electrode array near the modiolar wall. Thus, cells embedded within the modiolar wall may be stimulated at a lower energy setting than would be required if the electrode contacts were not facing the modiolar wall. Such an electrode array placement achieves the desired stimulation at the lowest possible power levels. The electrode design of the present invention, however, is adaptable and, as shown in FIG. 2, can be made with an electrode array with a wider arc. The electrode array of FIG. 2, which is used to deeply insert the electrode array between about 1.5 and 2.0 turns in the cochlea, will tend to uncurl with greater pressure applied between the lead and lateral wall of the scala tympani. A wider arc for the curvature is better suited to an electrode array which is very long, and this particular embodiment has a very thin and super-flexible tip optimal for deep, lateral placement, because such a wider arc can prevent jamming or sticking while the electrode array is being inserted into the cochlea. In either embodiment of the lead of the present invention, the lead can be placed into the cochlea very gently to avoid damage to the cochlear walls. It is thus seen that a lead is provided that has enhanced performance and that is easily assembled.

While the invention herein disclosed has been described by means of specific embodiments and applications thereof, numerous modifications and variations could be made thereto by those skilled in the art without departing from the scope of the invention set forth in the claims.

What is claimed is:

1. An implantable lead for use with electrical stimulation, the lead comprising:
   a flexible carrier having a proximal end, a distal end, a medial side and a lateral side; a distal, pre-curved lead section having memory;
   a plurality of electrode contacts embedded at the distal end of the lead, which electrode contacts comprise an electrode array;
   a plurality of conductor wires embedded in the carrier, each conductor wire connected to at least one electrode contact;

a longitudinal stylet insertion channel in the carrier extending into at least a part of the distal, pre-curved lead section;

an overmold which caps the opening of the stylet channel and wherein the overmold has a slit opening; and a pin plug which has a head and a curved tail pin, which pin plug is dimensioned and configured to permit the pin plug to be inserted head first into the overmold slit opening to seal the slit opening;

wherein the overmold has a cross-configured slit for allowing an insertion stylet to be inserted into the stylet insertion channel.

2. A method of implanting an implantable stimulation lead having an insertion stylet channel with a channel opening on the lead body, the method comprising:

(a) implanting the lead using the stylet;
(b) withdrawing the stylet from the lead; and
(c) capping the insertion stylet channel opening,
wherein capping the channel opening is accomplished by taking a pin plug, having a head and curved pin, and inserting the head of the pin plug into the lead to seal the channel opening.

3. A cochlear lead system comprising:
a cochlear lead including:
a flexible carrier having a proximal end and distal end;
a stylet insertion channel incorporated into the flexible carrier; and
an electrode array placed on the distal lead end;
a pin plug for capping the insertion stylet, the pin plug having a head and tail pin with a curvature in the tail pin; and
an insertion tool which has a first end and second end, wherein the first end has a pin plug holding channel that accommodates the tail pin and holds it within the holding channel with a friction fit.

4. An implantable lead for use with electrical stimulation, the lead comprising:

a flexible carrier having a proximal end, a distal end, a medial side and a lateral side;

a distal, pre-curved lead section having memory;

a plurality of electrode contacts embedded at the distal end of the lead, which electrode contacts comprise an electrode array;

a plurality of conductor wires embedded in the carrier, each conductor wire connected to at least one electrode contact;

a longitudinal stylet insertion channel in the carrier extending into at least a part of the distal, pre-curved lead section;

an overmold which caps the opening of the stylet channel and wherein the overmold has a slit opening; and a pin plucg which has a head and a curved tail pin, which pin plucg is dimensioned and configured to permit the pin plucg to be inserted head first into the overmold slit opening to seal the slit opening, wherein the most distal tip of the lead that includes a subset of the electrode array is constructed as a super-flexible tip; and wherein the super-flexible tip does not include the stylet insertion channel and which super-flexible tip has a substantially smaller thickness than the remainder of the distal lead containing the electrode array that is not super-flexible.

5. The lead of claim 4, wherein the distal end of the lead is dimensionally tapered and sized so that the lead can be implanted no greater than about 2 turns inside the cochlear duct, which duct is the scala tympani.

6. The lead of claim 4, wherein the overmold has a cross-configured slit for allowing an insertion stylet to be inserted into the stylet insertion channel.

* * * * *